United States Patent
Knowles et al.

(10) Patent No.: US 8,258,081 B2
(45) Date of Patent: Sep. 4, 2012

(54) USE OF C3 TO C14 ALIPHATIC ALDEHYDES, KETONES AND PRIMARY AND SECONDARY C3 TO C7 ALIPHATIC ALCOHOLS TO INHIBIT SPROUTING OF POTATO TUBERS

(75) Inventors: Norman Richard Knowles, Pullman, WA (US); Lisa O'Rear Knowles, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 1002 days.

(21) Appl. No.: 12/186,861

(22) Filed: Aug. 6, 2008

(65) Prior Publication Data
US 2009/0062126 A1    Mar. 5, 2009

Related U.S. Application Data

(60) Provisional application No. 60/955,156, filed on Aug. 10, 2007.

(51) Int. Cl.
*A01N 35/00* (2006.01)
*A01N 31/02* (2006.01)
*G01N 33/64* (2006.01)
*G01N 33/98* (2006.01)
*A01P 21/00* (2006.01)

(52) U.S. Cl. ......... 504/348; 504/353; 436/128; 436/131
(58) Field of Classification Search .................. None
See application file for complete search history.

(56) References Cited

U.S. PATENT DOCUMENTS

| | | | | |
|---|---|---|---|---|
| 3,159,476 | A * | 12/1964 | Young | 504/353 |
| 3,852,057 | A * | 12/1974 | Findley et al. | 504/184 |
| 3,853,532 | A * | 12/1974 | Rein et al. | 504/184 |
| 5,436,226 | A * | 7/1995 | Lulai et al. | 504/291 |
| 6,855,669 | B2 | 2/2005 | Knowles et al. | |
| 2004/0053787 | A1 * | 3/2004 | Knowles et al. | 504/348 |
| 2007/0087446 | A1 | 4/2007 | Gebler et al. | |

OTHER PUBLICATIONS

Bradow, J. M.; Connick, W. J., Jr.; Journal of Chemical Ecology, 1990, v. 16, iss. 3, 645-666.*
International Search Report dated Oct. 22, 2008 (1 page).

* cited by examiner

*Primary Examiner* — Johann Richter
*Assistant Examiner* — Erin Hirt

(57) ABSTRACT

Compositions and methods for inhibiting the sprouting of potato tubers are provided. The compositions comprise C3 to C14 aliphatic aldehydes and ketones, and/or C3 to C7 primary and secondary aliphatic alcohols.

5 Claims, 4 Drawing Sheets

US 8,258,081 B2

USE OF C3 TO C14 ALIPHATIC ALDEHYDES, KETONES AND PRIMARY AND SECONDARY C3 TO C7 ALIPHATIC ALCOHOLS TO INHIBIT SPROUTING OF POTATO TUBERS

CROSS-REFERENCE TO RELATED APPLICATIONS

This application claims benefit of U.S. provisional patent application 60/955,156, filed Aug. 10, 2007, the complete contents of which is hereby incorporated by reference.

BACKGROUND OF THE INVENTION

1. Field of the Invention

The invention generally relates to using C3 to C14 aliphatic aldehydes and ketones, and C3 to C7 aliphatic primary and secondary alcohols to inhibit sprouting when applied to potato tubers.

2. Background of the Invention

Following harvest, potato tubers undergo a natural period of dormancy during which sprout growth is inhibited by endogenous hormones. As tubers emerge from dormancy and begin to sprout, respiration increases, starch is catabolized to sugars, and weight loss increases. The result is a decrease in quality of tubers destined for fresh and processing markets. Hence, inhibition of sprouting through chemical or physical means preserves quality and prolongs the duration of storage.

The sprout inhibitors registered for use on potatoes in the United States are CIPC (also known as chlorpropham, Sprout Nip®, etc.), maleic hydrazide (MH), DMN (also known as dimethylnaphthalene, 1,4SIGHT®, 1,4SEED®, 1,4SHIP®), DIPN (diisopropylnaphthalene, Amplify®), and clove oil (Biox-C®; Sprout Torch™). Except for MH, which is applied pre-harvest to actively growing plants, all inhibitors are applied post harvest when tubers are in the storage bin.

CIPC is the most effective and most widely used potato sprout inhibitor. The chemical is most often applied as a thermal aerosol fog into potato storages after wound-healing and prior to sprouting. In the Pacific Northwest, this is usually in November or December, before dormancy has ended. The chemical is fogged into storage at the recommended rate of 1 lb chlorpropham/600 cwt. One gallon of CIPC aerosol grade will treat 4200 cwt (210 tons) of potatoes. CIPC can inhibit sprouting and extend the storage life of table-stock and processing potatoes for up to 1 year with two applications.

CIPC is an effective sprout suppressant that has been used in the potato industry for about 40 years and the EPA considers it as a group E chemical (non-carcinogenic). CIPC was originally registered in the United States as a pre- and post-emergence herbicide in 1962 and the EPA has set residue limits for potato tubers. Notwithstanding its safety record, the trend today is to reduce the use of synthetic pesticides in agriculture in order to reduce residues in the world's food supply. The chemical is continually being scrutinized by the EPA as it is among the three pesticides found in the highest concentrations in the average American diet (Gartrell, M. J., J. C. Craun, D. S. Podrebarac, and E. L. Gunderson. 1986. Pesticides, selected elements, and other chemicals in adult total diet samples October 1980-March 1982. J. Assoc. Off. Anal. Chem. 69:146-161). CIPC constitutes over 90% of the total synthetic residues found in U.S. potatoes (Gartrell et al., 1986). The EPA recently issued a re-registration eligibility decision for CIPC and dropped the tolerance level for residues on potatoes. The economic importance of this chemical as a sprout inhibitor to the potato industry is illustrated by the fact that the registrants spent over $6,000,000 in this re-registration process. While other potential sprout suppressants have been identified (e.g. aromatic aldehydes and alcohols, methylesters of rape oil, carvone, jasmonates, spearmint and peppermint oils), none appear as effective as CIPC. A need thus exists to identify and develop the most benign chemicals possible (ideally natural, phytochemicals) that are effective as sprout inhibitors.

1,4SIGHT® (94.7% DMN=1,4-dimethylnaphthalene) is one such natural chemical that is also registered for sprout control, but it tends to be less effective than CIPC. DMN is naturally produced in potatoes. It is more volatile than CIPC and thus dissipates from tubers more rapidly than CIPC. Multiple applications of DMN are required to maintain season-long sprout inhibition. DMN is vaporized and applied as an aerosol into bulk storages. It can be applied any time after tubers are placed in the bin but is usually applied later in the fall or early winter when sprouting potential begins to increase. DMN is registered for use at a rate of 1 lb DMN/500 cwt (=20 ppm on a DMN to potato weight basis). Because of the need for multiple applications of DMN to achieve prolonged inhibition of sprouting, DMN is more costly to use than CIPC.

Other natural volatile sprout inhibitors have been identified. Carvone (derived from caraway seed) is commercially available for use on potatoes in the Netherlands (Hartmans, K. J., P. Diepenhorst, W. Bakker and L. G. M. Gorris. 1995. The use of carvone in agriculture—sprout suppression of potatoes and antifungal activity against potato-tuber and other plant-diseases. Industrial Crops and Products 4:3-13). The following US patents describe the use of various compounds for the inhibition of potato sprout formation: U.S. Pat. No. 5,436,226 to Lulai, et al. (Jul. 25, 1995) describes the use of jasmonates; U.S. Pat. No. 5,580,596 to Winkelmann et al. (Dec. 3, 1996) describes the use of rape oil and certain long-chain alcohols, either alone or in combination; U.S. Pat. No. 5,139,562 to Vaughn et al., (Aug. 16, 1992) describes the use of volatile monoterpenes (e.g. from eucalyptus, peppermint, spearmint, etc.); and U.S. Pat. No. 5,129,951 to Vaughn et al., (Jul. 14, 1992) describes the use of aromatic aldehydes and alcohols. In addition, Vokou et al. (1993) have demonstrated that the essential oils from a multitude of herbs (e.g. sage and rosemary) possess sprout inhibiting activity in potatoes.

There remains an ongoing need to provide alternative sprout inhibitors that are safe and effective, particularly sprout inhibitors that are natural compounds, and that do not pose a threat to the environment or to the health of humans and other species.

SUMMARY OF THE INVENTION

A novel method for inhibiting (e.g. preventing, forestalling, slowing, reversing, or otherwise hindering) the development of sprouts in potato tubers is provided. The method includes the step of exposing potato tubers to one or more C3 to C14 aliphatic aldehydes or ketones, and/or to C3 to C7 aliphatic primary or secondary alcohols to inhibit sprouting of the tubers. Examples of such compounds include 2-nonanone, nonanal, 2-heptanol, and trans-2-hepten-1-ol and analogous aliphatic compounds of 3 to 14-carbons in the case of aldehydes and ketones, or 3 to 7 carbons in the case of primary or secondary alcohols.

The compounds may be applied directly to potato tubers. Alternatively, the compounds may be derived from the breakdown of C3 to C14 α,β-unsaturated aldehydes and ketones such as those described in U.S. Pat. No. 6,855,699 to Knowles et al. (Feb. 15, 2005). U.S. Pat. No. 6,855,699 describes the use of C3 to C14 α,β-unsaturated aldehydes and ketones, many of which are naturally produced in fruits and vegetables, to inhibit the sprouting of potato tubers. However, it has been discovered that the breakdown products of these C3 to C14 α,β-unsaturated aldehydes and ketones, including the compounds described herein, are also useful for this purpose.

In addition, the invention provides methods for detecting the appearance of the metabolites of C3 to C14 α,β-unsaturated aldehydes and ketones in or on potato tubers to which they have been applied. Such methods involve measuring an amount or level of C3 to C14 aliphatic aldehydes or ketones, and/or C3 to C14 aliphatic primary or secondary alcohols, in order to track or monitor the breakdown or catabolism of the C3 to C14 α,β-unsaturated aldehydes and ketones.

DETAILED DESCRIPTION OF THE PREFERRED EMBODIMENTS OF THE INVENTION

Figure 1:
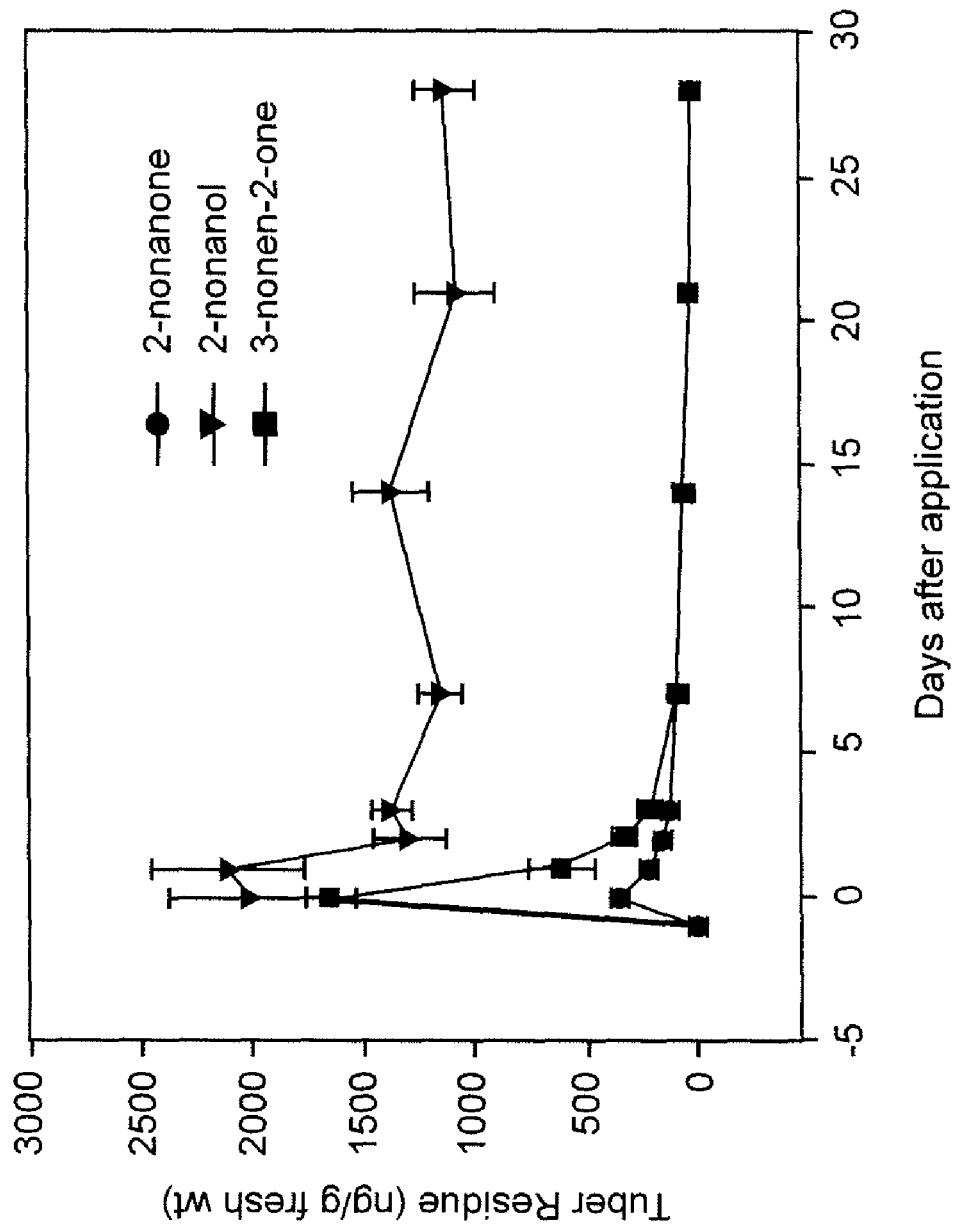
FIG. 1. Levels of 3-nonen-2-one, 2-nonanone, and 2-nonanol in tubers initially treated with 0.75 mmol/kg 3-nonen-2-one and stored at 9° C. Content of residues in the outer 20 mm of tuber.

The present invention is based on the discovery that C3 to C14 aliphatic aldehydes and ketones, and/or C3 to C7 aliphatic primary and secondary alcohols, function to inhibit the development of potato sprouts. These compounds have been identified as metabolites of the previously known potato tuber sprout inhibitors C3 to C14 α,β-unsaturated aldehydes and ketones, and have certain advantages in terms of production, use and performance. Many of the compounds offer the advantage of being naturally occurring and thus relatively safe and nontoxic to use. These compounds may be used alone or in combination with each other, or in combination with other known tuber sprout inhibitors, pesticides and growth regulators.

Aliphatic C3 to C14 aldehydes that may be used in the practice of the invention generally have the chemical formula

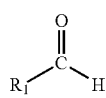

where $R_1$ is a C2 to C13 branched or unbranched, substituted or unsubstituted saturated alkyl or a C2 to C13 branched or unbranched, substituted or unsubstituted unsaturated alkenyl. In some embodiments of the invention, the aldehyde is nonanal,

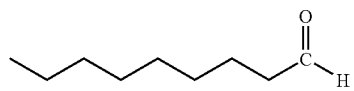

or decanal,

Aliphatic C3 to C14 ketones that may be used in the practice of the invention generally have the chemical formula

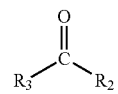

where $R_2$ is a C1 to C12 branched or unbranched, substituted or unsubstituted saturated alkyl or a C1 to C12 branched or unbranched, substituted or unsubstituted unsaturated alkenyl, and $R_3$ is a C1 to C12 branched or unbranched, substituted or unsubstituted saturated alkyl or a C1 to C12 branched or unbranched, substituted or unsubstituted unsaturated alkenyl. $R_2$ and $R_3$ may be the same or different. In some embodiments of the invention, the ketone is 2-nonanone,

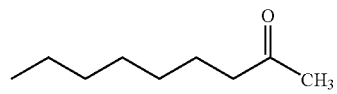

or 3-decanone,

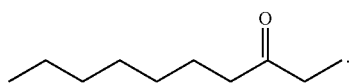

Aliphatic C3 to C7 primary alcohols that may be used in the practice of the invention generally have the chemical formula

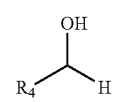

where $R_4$ is a C2 to C6 branched or unbranched, substituted or unsubstituted saturated alkyl or a C2 to C6 branched or unbranched, substituted or unsubstituted unsaturated alkenyl. In various embodiments of the invention, the unsaturated C3 to C7 primary alcohol is 1-hexanol,

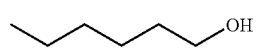

1-heptanol,

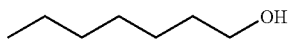

trans-2-hexen-1-ol,

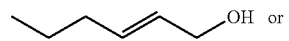 or trans-2-hepten-1-ol,

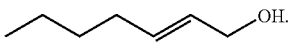

The aliphatic C3 to C7 secondary alcohols that may be used in the practice of the present invention generally have the chemical formula

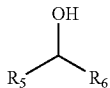

where $R_5$ is a C1 to C5 branched or unbranched, substituted or unsubstituted saturated alkyl or a C1 to C5 branched or unbranched, substituted or unsubstituted unsaturated alkenyl. R6 is a C1 to C5 branched or unbranched, substituted or unsubstituted saturated alkyl or a C1 to C5 branched or unbranched, substituted or unsubstituted unsaturated alkenyl. $R_5$ and $R_6$ may be the same or different. In one embodiment of the invention, the saturated C3 to C7 secondary alcohol is 2-heptanol,

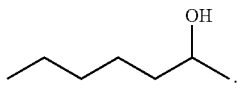

Examples of additional compounds that may be used in the practice of the invention include but are not limited to the following:

Aliphatic C3 to C14 aldehydes that may be used in the practice of the present invention include but are not limited to: propanal, butanal, pentanal, hexanal, heptanal, octanal, 4-nonenal, 6-nonenal, decanal, undecanal, dodecanal, tridecanal, and tetradecanal.

Aliphatic C3 to C14 ketones that may be used in the practice of the present invention include but are not limited to: propanone, 2-butanone, 2-pentanone, 2-hexanone, 2-heptanone, 2-octanone, 3-octanone, 3-nonanone, 2-decanone, 3-decanone, 2-undecanone, 2-dodecanone, 2-tridecanone, and 2-tetradecanone.

Aliphatic C3 to C7 primary alcohols that may be used in the practice of the present invention include but are not limited to: 1-propanol, 1-butanol, 2-buten-1-ol, 1-pentanol, 2-penten-1-ol, 1-hexanol, 2-hexen-1-ol, and 1-heptanol.

Aliphatic C3 to C7 secondary alcohols that may be used in the practice of the present invention include but are not limited to: 2-propanol, 2-butanol, 2-pentanol, and 2-hexanol.

By "substituted" we mean the replacement of hydrogen with a monovalent or divalent radical. Suitable substitution groups include but are not limited to, for example, hydroxyl, nitro, amino, imino, cyano, halo, thio, thioamido, amidino, imidino, oxo, oxamidino, methoxamidino, guanidino, sulfonamido, carboxyl, formyl, lower alkyl, halo-lower alkyl, lower alkoxy, halo-lower alkoxy, lower alkoxyalkyl, alkylcarbonyl, cycloalkyl, heterocycloalkyl, alkylthio, aminoalkyl, cyanoalkyl, and the like.

The application of sprout inhibiting compounds to potato tubers is generally known to those of skill in the art. The treatment of potato tubers is described, for example, in U.S. Pat. No. 6,855,669 (Knowles et al.), the complete contents of which are hereby incorporated by reference. Application is typically to bulk potatoes in storage bins, although this need not be the case as the compounds may be applied to potatoes stored or sorted in any manner, so long as sufficient contact is made between the compounds and the potato tubers to inhibit sprouting. Application of the compounds to the potatoes may be carried out by any of several methods. Generally, the compound(s) will be volatilized, e.g. by cold fogging, or at high temperature to create a thermal fog, or by atomization, and introduced into storage bins e.g. via the ventilation system. This introduction may be a discrete event that is carried out once or multiple times throughout the storage period. Alternatively, a slow-release mechanism or formulation may be employed in which the compound gradually enters the storage area over a longer period of time, for example by evaporation from a source impregnated with the compound(s). Further, the compounds may also be advantageously applied by spraying or misting a liquid form of the compound onto the potatoes, or by dipping or otherwise coating the potatoes with the compound, either prior to, during, or after the potatoes are stored (e.g. between storage and boxing or bagging for commercial purposes). Such compounds can also be used to coat or impregnate consumer containers (such as cardboard boxes, burlap bags, plastic bags etc) which typically hold potatoes coming out of storage sheds or bins for the express purpose of making available the precursor or metabolite compounds to delay sprouting in transit and at final destinations (e.g. homes, grocery stores, restaurants and other food establishments). For such applications, the compounds may also be mixed with various other agents known to facilitate the delivery of gases. liquids, or gels as appropriate (e.g. emulsifiers, slow release agents or matrices and the like).

The timing of exposure of the potatoes to the compounds of the invention can be prior to or after emergence from dormancy.

The application of the compounds may be carried out only once as described above (i.e. early in the storage of the potatoes). Alternatively, depending on the factors such as the cultivar, the time of harvest of the potatoes, the length of storage of the potatoes, the fate of the potatoes, etc. multiple applications of the compounds may be made. For example, if the potatoes are to be used as seed potatoes, only one application may be necessary as the eventual sprouting of the potatoes will be desirable. However, if the potatoes are to be stored long term (e.g. over the entire winter for distribution in the spring or the following summer) multiple applications may be made. In this case, the first application will generally be made early in the storage process (e.g. at between 4 and 32 weeks following harvest), and subsequent applications may also be made at roughly 4 to 12 week intervals as needed, until the potatoes are retrieved for use.

The amount of compound (or compounds) that is applied is sufficient to terminate, slow, prevent, and/or inhibit sprout growth on the potato tubers. The development of sprouts may thus be prevented altogether, or the onset of sprouting may be delayed, or existing sprouts may be killed, or the development of sprouts may be slowed compared to untreated tubers, etc. In any case, the process of sprouting is, in general, inhibited by treating the potato tubers with the compounds as described herein, or with their precursor compounds (e.g. see U.S. Pat. No. 6,855,669, for examples of precursor α,β-unsaturated aldehydes and ketones which can be used to make the ketones and aldehydes and alcohols of this invention), in comparison to potato tubers that are not exposed to or contacted by the compounds in a similar manner. In general, such inhibition will result in a decrease in the number, length, or fresh weight of sprouts developing on the tubers, and/or a decrease in the rate of growth (as determined by length, number, and/or weight) of sprouts that develop on the treated tubers, in comparison to potato tubers that are not exposed to or contacted by the compounds. The decrease will be in the range of at least about 10 to 100%, preferably in the range of about 50 to 100%, and most preferably in the range of about 75 to 100%. Thus, the treated tubers will display a decrease in sprout development of about 10, 20, 30, 40, 50, 60, 70, 80 90, or 100%, compared to untreated tubers.

The amount of a compound (or mixture of compounds) that is used to inhibit sprouting according to the invention may vary from situation to situation. However, the amount will generally be in the range of from about 0.1 mmol/kg tuber fresh weight to about 3.0 mmol/kg tuber fresh wt.

According to the present invention, the compounds of the invention may be applied directly, or they may arise indirectly as metabolites from the application of precursor compounds such as, but not limited to, those described herein and in U.S. Pat. No. 6,855,669. The compounds of the invention may also be derived from the application of a formulation of an inactive chemically related species which is released as an active form upon application to tubers. Examples of this chemistry are an acetal or hemiacetal of the active aldehyde or the ketal or hemiketal of the active ketone. The compounds may be applied in combination with other agents used to treat potatoes, examples of which include but are not limited to other substances that also inhibit sprouting. In this case, the use of the compounds of the present invention may allow the use of less of another substance whose use is less desirable (e.g. a substance that is not naturally occurring, is more expensive, toxic, etc). Such combinations may also allow the use of lower doses of the compounds of the present invention.

The preparation of the compounds for use in the practice of the present invention is known to those of skill in the art. Many of the compounds are commercially available. Others may be synthesized by well-known methods. Still others may be isolated from natural sources, e.g. from potatoes or other plants in which they are naturally produced, or in which their precursors are produced. Alternatively, the compounds may be produced in plants or other organisms that have been genetically engineered to overproduce the compounds. One advantage of the method of the present invention is that some of the compounds that are used in the method may be relatively inexpensive to procure, or can be expected to arise from the metabolism of relatively inexpensive α,β-unsaturated carbonyls that have been applied to potato tubers, and thus may offer an advantage when compared to more costly alternatives.

The invention includes methods for determining whether potato tubers have been previously exposed to C3 to C14 α,β-unsaturated aldehydes or ketones. The detection of prior exposure is important in identifying tubers treated with unregistered or illegally applied α,β unsaturated carbonyls that yield metabolites (for example C8-C14 alcohols). Such methods generally involve monitoring the conversion of C3 to C14 α,β-unsaturated aldehydes and C4 to C14 α,β-unsaturated ketones by detecting metabolites produced by the breakdown of these substances. The precursor compounds for which metabolites are of interest include those disclosed in U.S. Pat. No. 6,855,699. Such breakdown products occur regardless of the method of application of the precursor (e.g. cold fogging, thermal fogging, direct spray, slow release matrices, etc.). The precursors are applied in an amount sufficient to achieve or generate an inhibitory amount of metabolites.

Representative precursor C3 to C14 unsaturated aliphatic aldehyde parent molecules may be represented by the formula:

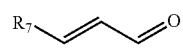

and the C4 to C14 unsaturated aliphatic ketone parent molecules may be represented by the formula

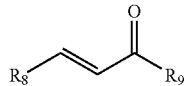

where $R_7$ is $H_2$ or a branched or unbranched, substituted or unsubstituted C1 to C11 lower alkyl, or branched or unbranched, substituted or unsubstituted C1 to C11 lower alkenyl. $R_8$ is $H_2$ or branched or unbranched, substituted or unsubstituted C1 to C10 lower alkyl, or branched or unbranched, substituted or unsubstituted C1 to C10 lower alkenyl. $R_9$ is branched or unbranched, substituted or unsubstituted C1 to C11 lower alkyl, or branched or unbranched, substituted or unsubstituted C1 to C11 lower alkenyl. Preferred aliphatic aldehydes for which breakdown products are traced include trans-2-pentenal; trans-2-hexenal; trans-2-heptenal; trans-2-octenal; trans-2-nonenal; trans-2-decenal; trans-2-undecenal; trans-2-dodecenal; trans, trans-2,4,-nonadienal; and trans-2, cis-6-nonadienal. Preferred aliphatic ketones for which breakdown products are traced include trans-3-hepten-2-one, trans-3-octen-2-one, trans-3-nonen-2-one, and trans-3-decen-2-one.

The breakdown products that are detected by the methods of the invention include, for example, aliphatic aldehydes having the chemical formula

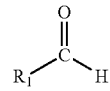

where $R_1$ is a C2 to C13 branched or unbranched, substituted or unsubstituted saturated alkyl or a C2 to C13 branched or unbranched, substituted or unsubstituted unsaturated alkenyl.

Ketones that may be detected in the practice of the invention generally have the chemical formula

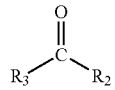

where $R_2$ is a C1 to C12 branched or unbranched, substituted or unsubstituted saturated alkyl or a C1 to C12 branched or unbranched, substituted or unsubstituted unsaturated alkenyl. $R_3$ is a C1 to C12 branched or unbranched, substituted or unsubstituted saturated alkyl, or a C1 to C12 branched or unbranched, substituted or unsubstituted unsaturated alkenyl. $R_2$ and $R_3$ may be the same or different.

Aliphatic C3 to C14 primary alcohols that may be detected in the practice of the invention generally have the chemical formula

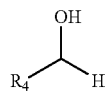

where $R_4$ is a C2 to C13 branched or unbranched, substituted or unsubstituted saturated alkyl or a C2 to C13 branched or unbranched, substituted or unsubstituted unsaturated alkenyl.

Aliphatic C3 to C14 secondary alcohols that may be detected in the practice of the present invention generally have the chemical formula

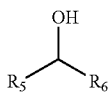

where $R_5$ is a C1 to C12 branched or unbranched, substituted or unsubstituted saturated alkyl or a C1 to C12 branched or unbranched, substituted or unsubstituted unsaturated alkenyl; and R6 is a C1 to C12 branched or unbranched, substituted or unsubstituted saturated alkyl or a C1 to C12 branched or unbranched, substituted or unsubstituted unsaturated alkenyl. $R_5$ and $R_6$ may be the same or different.

In a preferred embodiment, the metabolites of C3 to C14 α,β-unsaturated aldehydes include but are not limited to the primary alcohols, the aldehydes, and the α,β-unsaturated primary alcohols having the same carbon number as the parent compound. For example, trans-2-nonenal is expected to be metabolized to nonanal, 1-nonanol and trans-2-nonen-1-ol.

In other preferred embodiments, the metabolites of C4 to C14 α,β-unsaturated ketones include but are not limited to the saturated ketone or secondary alcohol having the same carbon number as the parent compound, and having the hydroxyl bound to the (former) carbonyl carbon of the parent compound. For example, trans-3-nonen-2-one is expected to be metabolized to 2-nonanone and 2-nonanol.

Preferred methods of detecting these metabolites include but are not limited to solvent extraction or solid phase microextraction of tuber tissue and analysis of the extract by, for example, high performance liquid chromatography-mass spectrometry or gas chromatography-mass spectrometry. Levels of breakdown products in potato tuber tissue will be dependent upon cultivar, length of exposure to the parent compound(s), storage time and storage temperature, etc. Generally, detection of the presence of one or more of the breakdown products at a level in the range of from about 14 ng/g fresh weight to about 1000 ng/g fresh weight, and preferably at least about twice the level present in non-treated potatoes, is sufficient to establish that potato tubers have previously been exposed to C3 to C14 α,β-unsaturated aldehydes and ketones. Those of skill in the art will recognize that control potatoes are typically potatoes that have not been exposed to C3 to C14 α,β-unsaturated aldehydes and ketones from exogenous sources, but which may naturally contain background levels of the metabolites of interest, which do occur naturally in potato tubers.

The following non-limiting examples serve to further illustrate the practice of the invention.

EXAMPLES

Example 1

Determination of the Metabolites of 3-nonen-2-one (3N2) and trans-2-nonenal (T2N)

The objective of this study was to determine the metabolites of 3-nonen-2-one (3N2) and trans-2-nonenal (T2N), which are two examples of α,β-unsaturated aldehydes and ketones that inhibit sprouting in potatoes as described in U.S. Pat. No. 6,855,669. Potato tubers were treated with 3N2 or T2N (0.75 mmol/kg tuber) for 24 h in a closed chamber. The chemicals were volatilized from filter paper inside the chamber. The tubers were removed from the treatment chamber and placed at 9° C. for up to 28 days.

Figure 2:
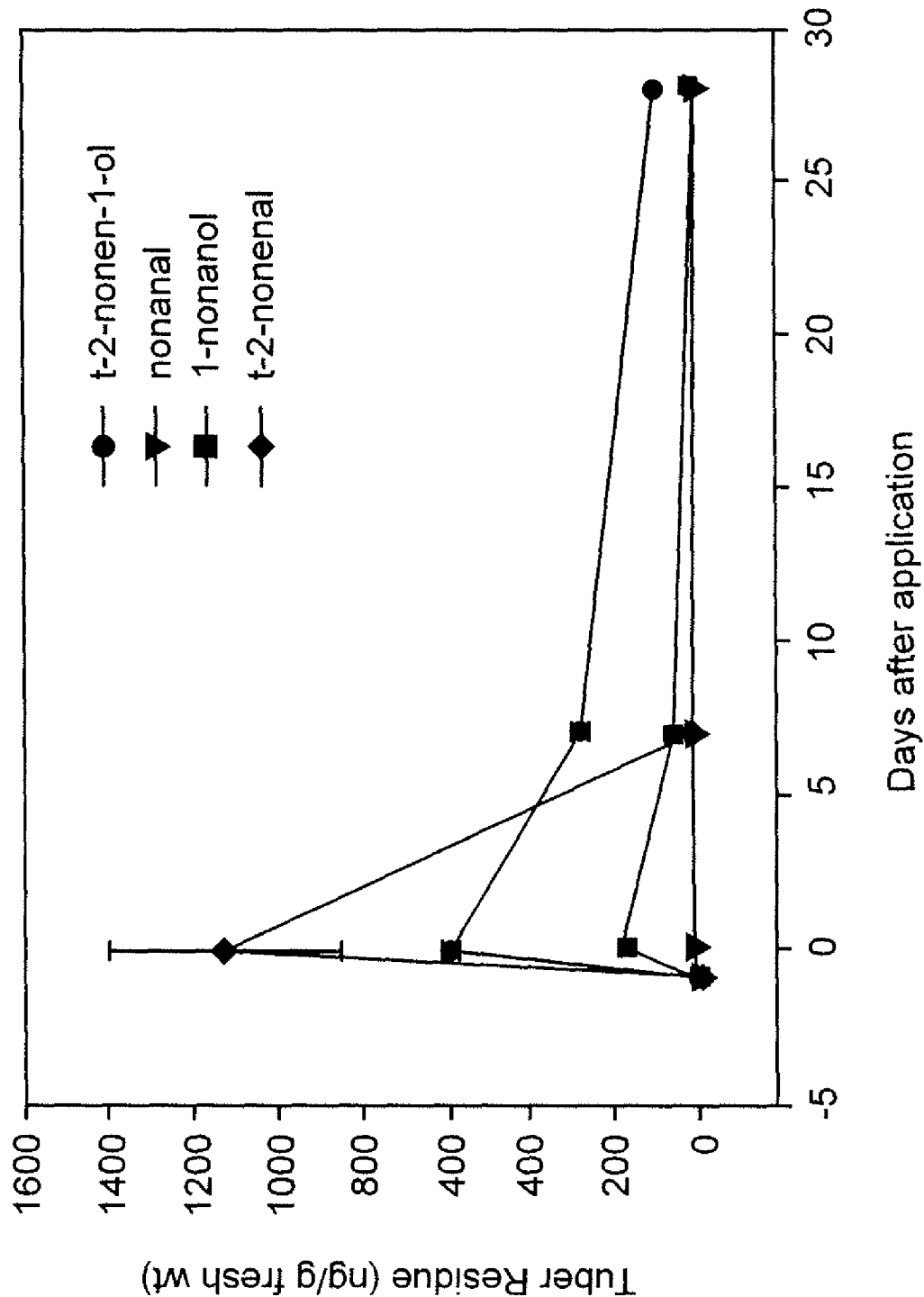
FIG. 2. Levels of trans-2-nonenal, nonanal, trans-2-nonen-1-ol and 1-nonanol in tubers initially treated with 0.75 mmol/kg trans-2-nonenal and stored at 9° C. Content of residues in the outer 20 mm of tuber.

Samples were taken for analysis of residues and metabolite identification over the 28-day storage period. FIG. 1 shows that the tubers metabolized the 3N2 to 2-nonanone and 2-nonanol. 2-Nonanol was the most persistent, maintaining a 1.2 ppm residue in the outermost 20 mm of tubers through 28 days following treatment with 3N2 (FIG. 1). When tubers were treated similarly with T2N, the metabolites were trans-2-nonen-1-ol, nonanal and 1-nonanol (FIG. 2). The trends in residue levels were similar to that of 3N2 and the most persistent metabolite was trans-2-nonen-1-ol.

Example 2

Use of Nonanal, 1-nonanol, and trans-2-nonen-1-ol as Inhibitors of Sprouting of Potato Tubers The objective of this study was to determine the extent to which nonanal, 1-nonanol, and trans-2-nonene-1-ol (metabolites of T2N) inhibit sprouting of potato tubers relative to T2N. Tubers were treated separately with 0.25, 0.5 and 0.75 mmol/kg of T2N, nonanal, 1-nonanol, and trans-2-nonene-1-ol for 24 h as described in Example 1. The treated tubers were placed at 19° C. and sprout fresh weights were measured 21 days after treatment. The percentage inhibition of sprouting relative to untreated control tubers is shown in Table 1. T2N inhibited sprouting (100%) at all concentrations. Nonanal and 1-nonanol inhibited sprouting by 13 to 51%, depending on the compound and the concentration that was used.

TABLE 1

Effects of 9-carbon aliphatic aldehydes and primary alcohols on sprouting of potato tubers.

| | mmol/kg tubers | | |
| --- | --- | --- | --- |
| | 0.25 | 0.5 | 0.75 |
| Inhibitor | % Inhibition | | |
| trans-2-nonenal | 100 | 100 | 100 |
| nonanal | 13.2 | 32.1 | 17.0 |
| 1-nonanol | 28.3 | 24.5 | 50.9 |
| trans-2-nonen-1-ol | 8.9 | 62.8 | 31.6 |

Example 3

Use of 2-nonanone and 2-nonanol as Inhibitors of Sprouting of Potato Tubers

The objective of this study was to determine the extent to which 2-nonanone and 2-nonanol (metabolites of 3N2) inhibit sprouting of potato tubers relative to 3N2. Tubers were treated separately as described in Example 1 with 0, 0.25, 0.5, and 0.75 mmol/kg of 3N2,2-nonanone, and 2-nonanol. The treated tubers were placed at 18° C. and sprout fresh weights were measured 21 days after treatment. All three compounds inhibited sprouting at 0.5 and 0.75 mmol/kg, relative to non-treated controls (Table 2). At 0.50 and 0.75 mmol/kg, 3N2 and 2-nonanone substantially inhibited sprout growth.

TABLE 2

Effects of 9-carbon aliphatic ketones and secondary alcohols on sprouting of potato tubers.

| | mmol/kg tubers | | |
|---|---|---|---|
| Inhibitor | 0.25 | 0.5 | 0.75 |
| | % Inhibition | | |
| 3-nonen-2-one | 99.6 | 99.9 | 99.9 |
| 2-nonanone | 77.22 | 97.9 | 98.8 |
| 2-nonanol | 65.1 | 79.8 | 72.9 |

Example 4

Figure 3:
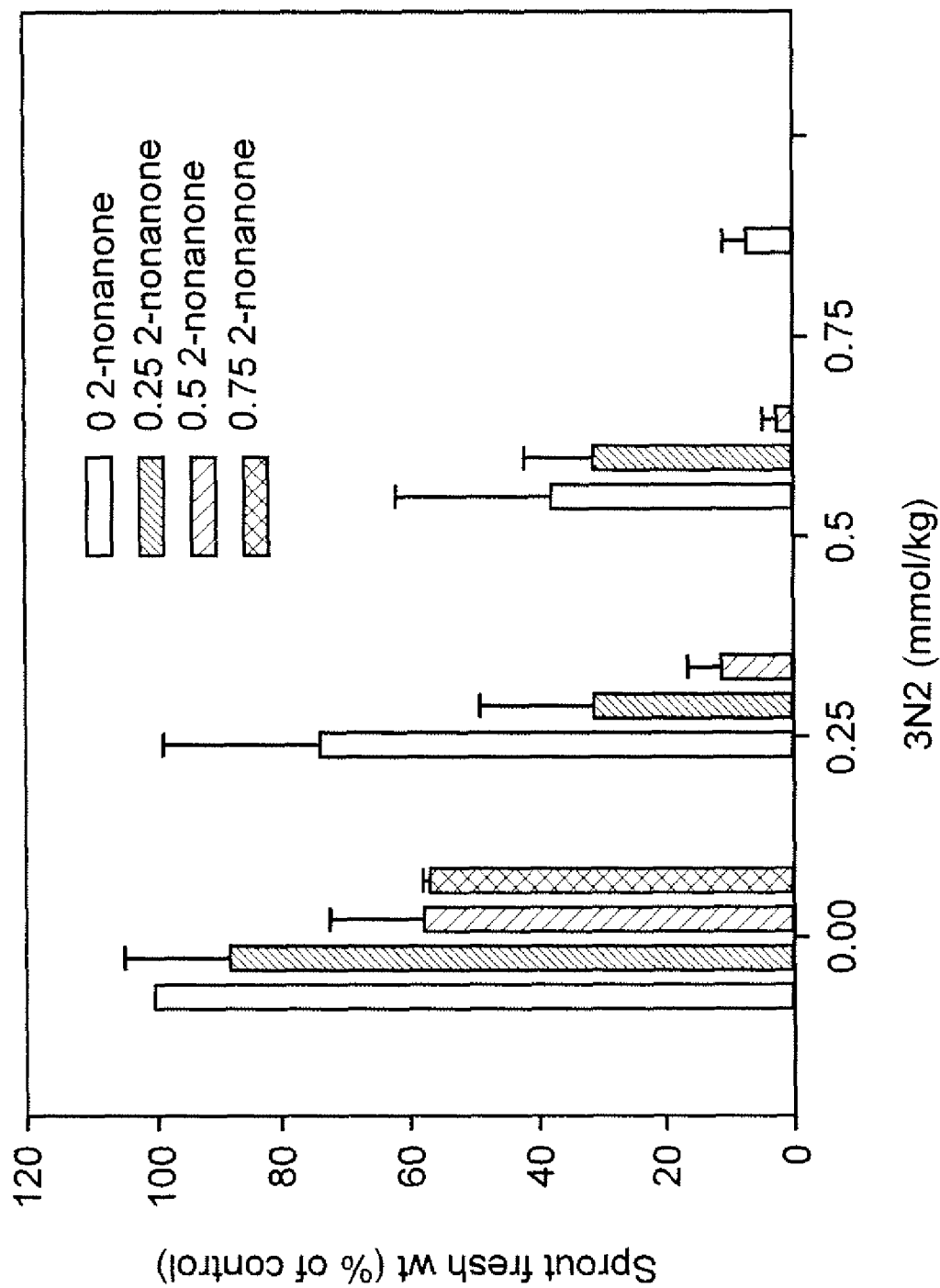
FIG. 3. Effects of 3-nonen-2-one (3N2) in various combinations with 2-nonanone on sprouting of Russet Burbank tubers. The compounds were applied as described in Example 1. Tubers were treated for 24 h, removed from treatment chambers, and placed at 22° C. to sprout for 3 weeks. Sprout fresh weight is expressed as a percentage of control (non-treated), which were 100% sprouted.

Use of Mixtures of 3N2 and 2-nonanone as Inhibitors of Sprouting of Potato Tubers The objective of this study was to determine the efficacy of mixtures of 3N2 and its metabolite, 2-nonanone, on sprout inhibition. Tubers were treated as described in Example 1 with 0 to 0.75 mmol/kg of 3N2 combined factorially with 0 to 0.75 mmol/kg of 2-nonanone. The treated tubers were placed at 22° C. and sprout fresh weights were measured 21 days after treatment. Sprout growth from tubers treated with 0.5 and 0.75 mmol/kg 2-nonanone averaged 58% of non-treated tubers, compared with 9% for 0.75% 3N2 applied alone (FIG. 3). The 0.25 mmol/kg 3N2+0.5 mmol/kg 2-nonanone treatment inhibited sprouting to the same extent as the 0.75 mmol/kg 3N2 treatment.

Example 5

Use of C3 to C7 Alcohols as Inhibitors of Sprouting of Potato Tubers

The objective of this study was to determine the extent to which 1-heptanol, 1-hexanol, 2-heptanol, trans-2-hepten-1-ol, trans-2-hexen-1-ol and 1-pentanol (C5 to C7 alcohols) inhibit sprouting of potato tubers. Tubers were treated separately with 0.25, 0.5, 0.75 or 1 mmol/kg of each alcohol for 24 h as described in Example 1. The treated tubers were placed at 18° C. and sprout fresh weights were measured 21 days after treatment. All compounds inhibited sprouting (Table 3). C7 alcohols inhibited sprouting by about 50 to about 100%, depending on the precise treatment.

TABLE 3

Effects of 5-7-carbon aliphatic primary and secondary alcohols on sprouting of potato tubers.

| | mmol/kg tubers | | |
|---|---|---|---|
| Inhibitor | 0.25 | 0.50 | 0.75 |
| | % Inhibition | | |
| 1-pentanol | 7.5 | 32.5 | 45.8 |
| 1-hexanol | 36.6 | 61.3 | 71.9 |
| 1-heptanol | 51.8 | 94.0 | 95.7 |
| trans-2-hexen-1-ol | 96 | 100.0 | 100.0 |
| trans-2-hepten-1-ol | 91.7 | 98.7 | 99.4 |
| 2-heptanol | 49.4 | 89.0 | 97.7 |

Example 6

Figure 4:
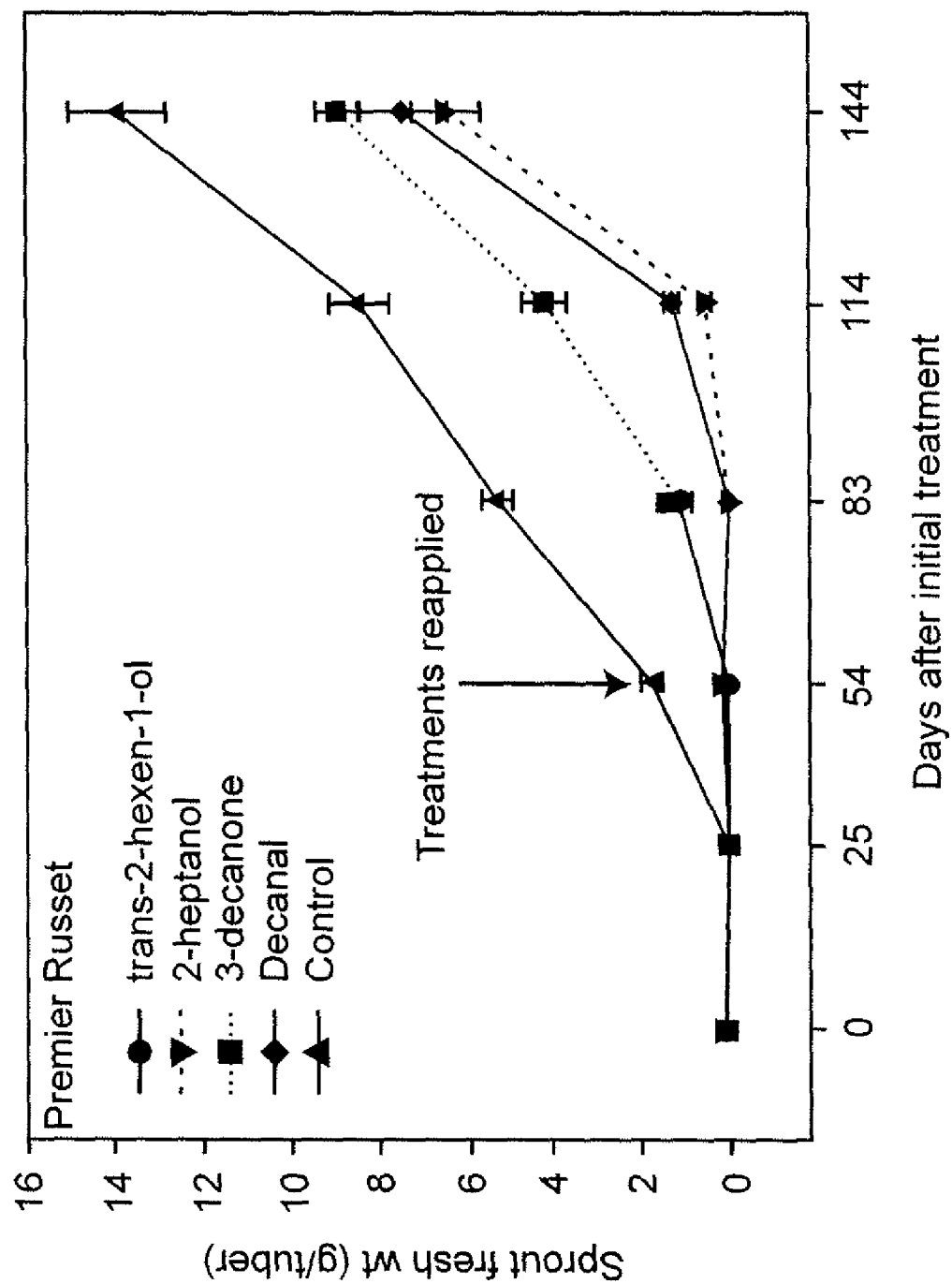
FIG. 4. Effect of trans-2-hexen-1-ol, 2-heptanol, decanal and 3-decanone on sprouting in Premier Russet tubers during long term storage at 9° C. Compounds were initially applied 98 days after harvest to tubers which had emerged from dormancy and displayed small (<3 mm) sprouts.

Use of an Aliphatic Aldehyde, an Aliphatic Ketone and Two Aliphatic Alcohols for Long Term Sprout Inhibition in Potato Tubers The objective of this study was to determine the extent to which trans-2-hexen-1-ol, 2-heptanol, decanal, and 3-decanone inhibit sprouting during extended storage under typical commercial storage conditions. Premier Russet tubers were treated separately with 0.75 mmol/kg of each compound in 190 L plastic barrels at room temperature. Chemicals were volatilized from filter paper within the barrels which were sealed for 24 hours during application. Tubers were then stored at 9° C. and sampled monthly to determine the amount of sprouting on a per tuber basis. All treatments were re-applied between the second and third month of storage. The sprout fresh weight per tuber of each of the treatments over time relative to untreated tubers is shown in FIG. 4. Trans-2-hexen-1-ol was eliminated from the study after 83 days due to excessive damage to the periderm, but sprouts were effectively controlled up to this point. 2-heptanol and decanal suppressed sprouting for 114 days (about 4 months of control). 3-decanone suppressed sprouting for 83 days.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for inhibiting sprouting of potato tubers, comprising the step of
   exposing said potato tubers to an amount of a composition sufficient to inhibit sprouting of said potato tubers, said composition comprising at least one of
   one or more C3 to C14 saturated aliphatic aldehydes; and
   one or more C3 to C14 saturated aliphatic ketones.

2. The method of claim 1, wherein said one or more C3 to C14 saturated aliphatic aldehydes has a chemical formula

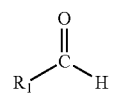

wherein $R_1$ is a C2 to C13 branched or unbranched, substituted or unsubstituted saturated alkyl.

3. The method of claim 2, wherein said one or more saturated aliphatic aldehydes is selected from the group consisting of nonanal,

and
decanal,

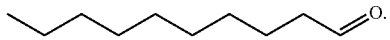

4. The method of claim 1, wherein said one or more C3 to C14 saturated aliphatic ketones has a chemical formula

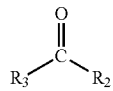

wherein each of $R_2$ and $R_3$ is C1 to C12 branched or unbranched, substituted or unsubstituted saturated alkyl, and wherein $R_2$ and $R_3$ may be the same or different.

5. The method of claim 4, wherein said one or more saturated aliphatic ketones is selected from the group consisting of 2-nonanone,

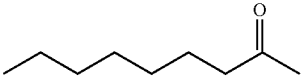

2-decanone,

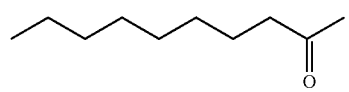

and
3-decanone,

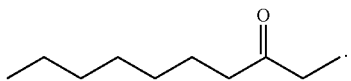

* * * * *